United States Patent [19]

Smith et al.

[11] Patent Number: 4,515,753

[45] Date of Patent: May 7, 1985

[54] INTEGRAL REAGENT DISPENSER

[75] Inventors: John L. Smith, New City; Vito F. Christiano, Port Chester, both of N.Y.

[73] Assignee: Technicon Instruments Corporation, Tarrytown, N.Y.

[21] Appl. No.: 441,880

[22] Filed: Nov. 15, 1982

[51] Int. Cl.³ .................. G01N 1/00; G01N 35/08
[52] U.S. Cl. .................. 422/102; 206/219; 422/82; 422/100; 422/63; 436/53
[58] Field of Search .......... 73/864.21, 864.22, 864.25, 73/864.12; 222/154; 206/219; 422/63, 64, 65, 81, 82, 102, 100; 436/43, 47, 52–54

[56] References Cited

U.S. PATENT DOCUMENTS

| | | | |
|---|---|---|---|
| 3,432,275 | 3/1969 | Unger | 422/102 |
| 3,449,081 | 6/1969 | Hughes | 422/100 X |
| 3,713,779 | 1/1973 | Sirago et al. | 206/219 X |
| 3,986,834 | 10/1976 | Steinbrink | 436/108 |
| 4,121,466 | 10/1978 | Reichler et al. | 73/864.22 |
| 4,332,768 | 6/1982 | Berglund | 422/63 |
| 4,357,301 | 11/1982 | Cassaday et al. | 422/64 |

Primary Examiner—Michael S. Marcus
Assistant Examiner—Michael S. Gzybowski
Attorney, Agent, or Firm—S. P. Tedesco; C. J. Herron

[57] ABSTRACT

The integral reagent dispenser disclosed comprises a reagent dispenser component provided with a reagent dispenser well having an opening adapted to present a liquid reagent for withdrawal therethrough and means to position a lens of liquid immiscible with said reagent between the reagent and the opening of said well. For example, the dispenser can have suitable dimensions and an inner surface which combine with the wetting characteristics of the reagent to form a concave reagent meniscus suitable to reliably position a lens of immiscible liquid thereon. The lens so formed is centrally located by the concave shape of the meniscus. Preferably, the reagent dispenser further includes an integrally associated source of reagent.

38 Claims, 10 Drawing Figures

FIG.10

INTEGRAL REAGENT DISPENSER

BACKGROUND OF THE INVENTION

1. Field of the Invention

The present invention relates to the field of reagent dispenser devices and packages, particularly those suitable for repeated introduction of reagents into automated analytical systems.

2. Brief Description of the Prior Art

Reagents are supplied to most analytical systems from separate reagent reservoirs by feed tubing. In many of these systems, the reagents are introduced into a fluid stream in a continuous flow conduit or into a reaction cuvette. The reservoirs are refilled from supply containers in which the reagent is shipped and stored. Some types of reagent storage containers use frangible or breakable capsules or ampules to hold lyophilized or otherwise dried reagent in combination with a reconstituting fluid. This lyophilized form provides the advantage of longterm stability and shelf life in stored reagent.

Some systems have used discrete reaction packages which include reagent sufficient for a single reaction. Sample is introduced and reacts with the reagent therein. Often, the portion of the package in which the reaction occurs is used in the system as an optical cuvette. This type of reaction vessel test pack is disclosed in U.S. Pat. No. Re. 29,725; U.S. Pat. No. 3,986,834; and U.S. Pat. No. 3,036,894. Another example of this type of apparatus is disclosed in U.S. Pat. No. 4,119,407. Certain of these devices provide for filtering capacity whereby reagent and/or sample are filtered prior to their introduction into a reaction chamber. This is disclosed, for example in U.S. Pat. No. 3,437,452.

None of these provides an integral package combining a stable storage/shipment container, reconstituting vessel, reagent reservoir and dispenser which delivers liquid reagent for repeated aspiration of reaction aliquots.

One of the most advanced types of analytical systems is a continuous flow system using conduits whose inner walls are coated with an immiscible liquid, such as the system described in Smythe et al, U.S. Pat. No. 3,479,141, assigned to the instant assignee, which discloses a transport system for automatic analysis apparatus in which a series of aqueous liquid samples are processed as a flowing fluid stream with substantially no contamination between segments. A fluoropolymer conduit and intersample carrier segments of silicone are used. This patent teaches that the silicone encapsulates the aqueous liquid segments, substantially completely eliminating the intermixing of successive liquid segments. Reagents are separately introduced on a continuous basis, e.g. in conventional fashion as described with respect to previous continuous flow systems.

In Smythe et al, U.S. Pat. No. 4,253,846, also assigned to the instant assignee, selective injection of reagent into a moving stream of sample segments is provided to such a continuous flow system and allows for an increase in the efficiency and throughput of sample processing. Using injectors such as poppet valves, the reagent is introduced by piercing the immiscible liquid layer encapsulating the selected sample segments. The immiscible liquid layer reforms after injection to maintain sample integrity and prevent carryover. Air and sample are alternately aspirated via a probe which periodically dips into a sample cup. The immiscible liquid is said to be introduced to the inlet end of the probe by an applicator (not shown) and aspirated along with air between successive sample immersions. The immiscible liquid can be a fluorocarbon and both the conduit wall and the poppet valve tip can be a fluorinated polymer. This patent does not further address the actual mechanism of immiscible liquid introduction and clearly indicates that it is separate from the "on-line" introduction of reagent.

Diebler et al, U.S. Pat. No. 4,121,466, also assigned to the instant assignee, disclose a metering apparatus useful to either dispense or aspirate sample. The surface of the aspirating probe is coated with an immiscible liquid film which, in the preferred embodiment, is flowed continuously down the peripheral probe surface at a rate substantially equal to the aspiration rate, so as to be eventually aspirated into the probe inlet. During immersion, excess immiscible liquid on the peripheral probe surface floats onto the surface of the liquid being aspirated but a small film remains on the probe surface. Also, during aspiration, a thin film of immiscible liquid continuously wets the interior probe surface. As the probe is withdrawn, the flow of immiscible liquid is commenced so as to be aspirated along the probe immediately upon withdrawal thereof from the liquid. Segments of the immiscible liquid and aspirated liquid are therefore successively passed along the probe system.

Smythe, U.S. Pat. No. 4,259,291, also assigned to the instant assignee, refers to the continuous flow systems described in the above Smythe et al and Diebler et al patents and addresses the need for more precise and uniform application of protective immiscible liquid coatings. An applicator directly surrounds the probe and layers a thin uniform film of immiscible liquid on the outer surface thereof. The applicator is moved relative to the probe to coat its outer surface. An aspirating mechanism connected to the probe alternately aspirates controlled volumes of air and aqueous sample therethrough. Immiscible liquid is said to be drawn into the probe along with the air segment so aspirated. Thus, alternating sample and air segments encased within the immiscible liquid are passed along the probe to a rotary valve which transfers each aspirated aqueous sample in turn from the probe to a conduit for dispensing to an analytical system. As described herein, a pool of wiped immiscible liquid forms about the probe due to the interplay of surface forces of the liquid in combination with the wetting forces of the immiscible liquid with the respect to the probe surface. When the sample cup is withdrawn from the probe, this pool forms a small globule of immiscible liquid over the inlet of the probe, inasmuch as it preferentially wets the probe material to the substantial exclusion of the aqueous sample. This patent teaches that the globule of immiscible liquid is aspirated into the probe inlet alaong with an air segment. Reagent is introduced "downstream" in a manner which is not further described.

Each of the above patents has provided an advance of one sort or another in the elimination of successive sample intermixing and carryover. This end has been widely recognized as a major consideration in the improvement of continuous flow systems. The combined references provide a significant background literature on the technology available to prevent interaction of segments in continuous flow analysis systems.

Nonetheless, none of these has provided an integral reagent dispenser which is adapted to control the introduction of precise volumes of immiscible liquids to analyzer systems of the continuous flow type. Continuous flow systems using conduits whose inner walls are coated with an immiscible liquid have not been previously available, and thus have not heretofore presented a need such as that addressed by the present invention.

SUMMARY OF THE INVENTION

A new concept in controlled fluid handling has been developed for use in a new generation of clinical chemistry analysis systems. These are continuous flow systems using conduits whose inner walls are coated with a probe accessed immiscible liquid. Controlled introduction of sufficient amounts of this immiscible liquid is critical for the proper operation of the system. This having now been recognized and the need addressed, the present invention provides an integral reagent dispenser which presents a liquid reagent and positions a lens of immiscible liquid for introduction into the system. The integral dispenser of this invention properly positions that immiscible liquid which replenishes the coating on the conduits of these continuous flow systems.

The integral reagent dispenser disclosed comprises a reagent dispenser component provided with a reagent dispenser well having an opening adapted to present a liquid reagent for withdrawal therethrough and means for positioning a lens of immiscible liquid between the surface of such reagent when contained in said well and the opening thereof. For example, the dispenser can have suitable dimensions and an inner surface, usually hydrophilic, which combine with the wetting characteristics of the reagent to form a concave reagent meniscus suitably reliable to position a drop of immiscible liquid thereon. In this embodiment, the dispenser well inner diameter is at most about that of the diameter of the lens plus twice the radius of the meniscus curvature, usually less than about 0.25 inch. So long as the well inner surface is fully wet by the reagent liquid, e.g. is hydrophilic in the preferred embodiment, the meniscus curvature is controlled by the surface tension of the particular reagent liquid in use. The drop of immiscible liquid forms a discrete lens (so-called because of its shape) due to the balance of interfacial tensions of the three fluids (reagent, immiscible liquid and air) at those points of three-phase contact which constitute the periphery of the lens. The lens so formed is centrally located by the concave shape of the meniscus. Preferably, the reagent dispenser further includes an integrally associated source of liquid reagent. The source of liquid reagent is, for example, a reagent reservoir having flexible side walls and a plurality of breakable capsules which are broken by external pressure on said side walls to reconstitute the contents thereof into a liquid reagent.

In a particularly preferred embodiment, the integral reagent dispenser of the invention comprises (a) a reagent dispenser assembly having a dispenser housing and, therein, first and second reagent dispenser components, each provided with a dispenser well having a hydrophilic inner surface and an inner diameter of less than about 0.25 inch; and (b) a reagent reservoir assembly having a reservoir housing and, therein, a first reservoir component containing at least one reagent of a composition effective to detectably react with a sample and associated with said first reagent dispenser to supply said at least one reagent thereto as a liquid; and a second reservoir component containing the remaining reagents of said composition and associated with said second reagent dispenser to supply said remaining reagent thereto as a liquid. In one example of this embodiment, each reservoir component includes a breakable capsule containing reagent, as described, in a lyophilized powder form as well as a breakable capsule containing a reconstituting liquid therefor.

This example of the preferred embodiment confers numerous advantages, including the long-term storage of unmixed ingredients and inherently secure packaging for shipping incorporated with a vessel for reconstitution, mixing and dispensing having a configuration adapted to present immiscible fluid and a plurality of related reagents for aspiration through an analyzer probe and to prevent contents spillage during rotation on an analyzer turntable. Further, the dispenser is integrally formed so as to prevent the risks of contamination and error inherent in manual reagent preparation and package refilling.

DESCRIPTION OF THE PREFERRED EMBODIMENTS

Although specific terms are used in the following description for clarity, they refer only to the particular embodiment(s) selected for illustration, and are not intended to limit the scope of the invention.

The reagent package of the present invention is particularly suitable for use in association with either batch type or continuous flow analyzers which aspirate sample(s), reagent(s) and immiscible liquid(s) through a probe assembly. Sample fluids on which tests are performed include biological, physiological, industrial, environmental and other types of liquids. Of particular interest are biological liquids such as whole blood, serum, plasma, urine, cerebrospinal fluid, broth and other culture media and supernatants as well as fractions of any of them. Each package holds at least some of the individual reagents of a conventional reagent composition known for the analysis of the above-described samples, in amounts sufficient for testing of a plurality of samples. The preferred immiscible liquid is one which preferentially wets the inner and outer probe surfaces and the inner wall surfaces of the conduits in the system to the substantial exclusion of all other fluids in the system and is usually a fluorocarbon.

Figure 1:
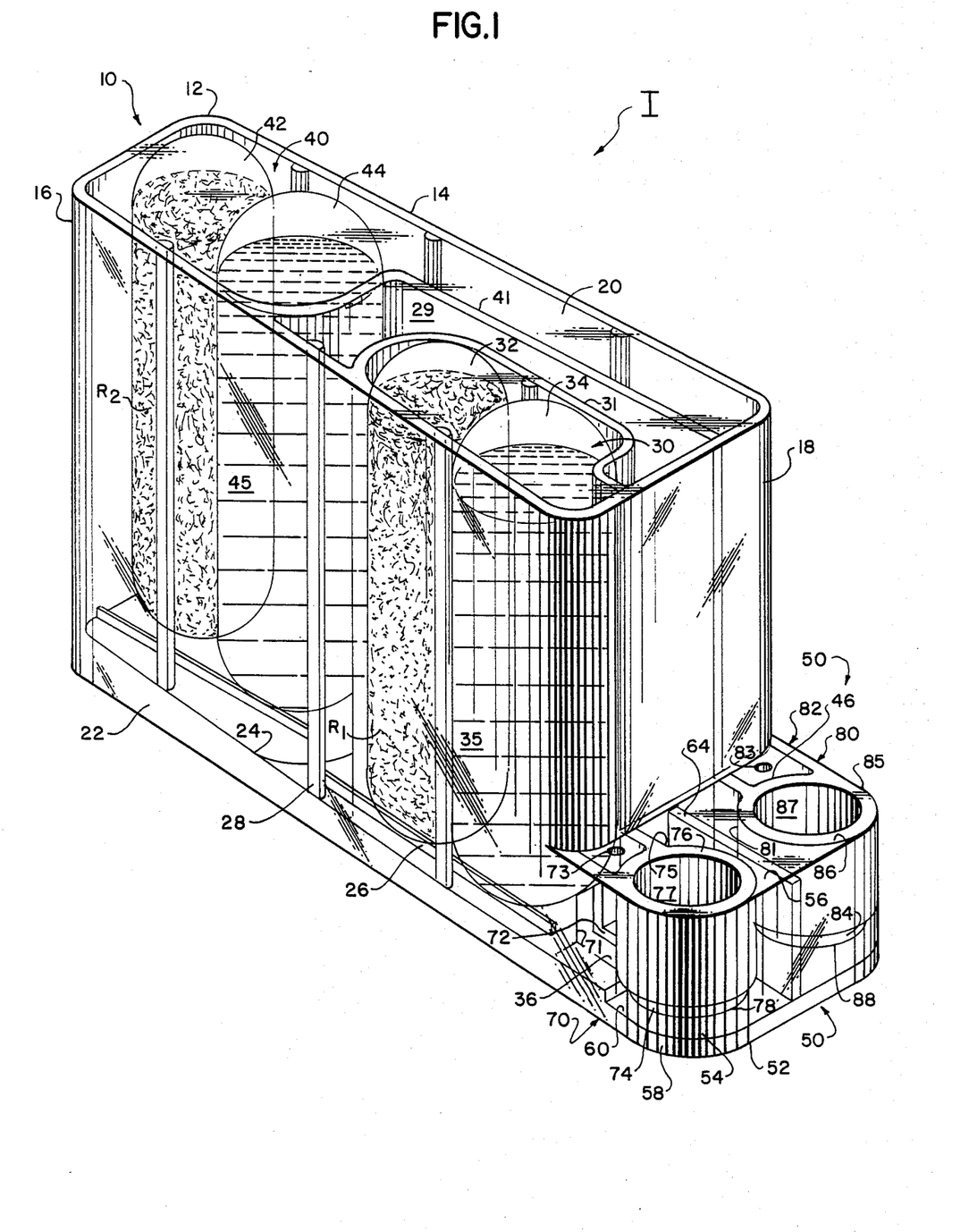
FIG. 1 is an isometric view of a preferred embodiment of the integral reagent dispenser in accordance with the invention.

Referring now to FIG. 1, a two-reagent reservoir/dispenser package I, as shown, contains separated portions of a complete reagent composition necessary for the analysis of a sample. Two-reagent reservoir/dispenser package I includes reagent reservoir assembly 10 having a reservoir housing 12 and a reagent supply component for each of the two reagents to be dispensed. Reservoir housing 12 includes integral flexible side walls 14 which are continuous with back wall 16, front wall 18 and top 20. Reservoir housing 12 is fixed to base 22 by conventional adhesive or bonding techniques to form an enclosure. Base 22 is provided with an inclined floor 24 to maximize availability of reagent contents, shard fins 26 to insure against occlusion of openings in the package, support ribs 28 which provide desired structural rigidity at selected portions of housing 12 and insulation chamber 29, within housing 12, which separates reagent supply components 30 and 40.

Reagent $R_1$ supply component 30 comprises component wall 31, reagent $R_1$ capsule 32, which is filled with lyophilized reagent $R_1$ powder, reconstituting liquid capsule 34 which is filled with reconstituting liquid 35 and a supply trough 36. Reagent $R_2$ supply component 40 is substantially identical to the above-described reagent supply component but for its position. As such, it comprises an enclosed component wall 41, reagent $R_2$ capsule 42 which contains lyophilized reagent $R_2$ powder, reconstituting liquid capsule 44 which contains reconstituting liquid 45, and supply trough 46. After appropriate package preparation, as described in detail below, supply component troughs 36 and 46 each deliver reconstituted liquid reagent to different components of a reagent dispenser assembly.

Still referring to FIG. 1, reagent dispenser assembly 50 includes a dispenser housing 52 and a dispenser component for each of the two reagents to be dispensed. Dispenser housing 52 includes housing wall 54, which forms an enclosure with top 56 and base 58. Base 58 is provided with a stepped floor 60, the step height of which is commensurate with the height of filter cups 78 and 88. Divider 64 separates the reagent dispenser components provided for each of the two reconstituted liquid reagents.

Reagent $R_1$ dispenser component 70 comprises a supply port 71, trough wall 72, vent hole 73, filter 74 and dispenser well 75, the interior of which is defined by dispenser well wall 76 having hydrophilic inner surface 77. As shown in later drawings, reagent $R_1$ which flows through supply port 71 is confined by trough wall 72 and thereby directed into the side of filter 74. From filter 74, it enters the interior of dispenser well 75, through the bottom, to present a standing volume of reagent $R_1$ liquid.

Reagent $R_2$ dispenser component 80 is substantially identical to the above-described reagent dispenser component but for its position and operates in the same manner. As such, it comprises a supply port 81, trough wall 82, vent hole 83, filter 84 and dispenser well 85, the interior of which is defined by dispenser well wall 86 having hydrophilic inner surface 87.

Dispenser wells 75 and 85 each has suitable dimensions which cooperate with the hydrophilic inner surfaces 77 and 87, respectively, and the wetting characteristics of the liquid therein to form a concave reagent reliably meniscus suitable to position a drop of immiscible liquid thereon as is more fully described with reference to later drawings.

Figure 2:
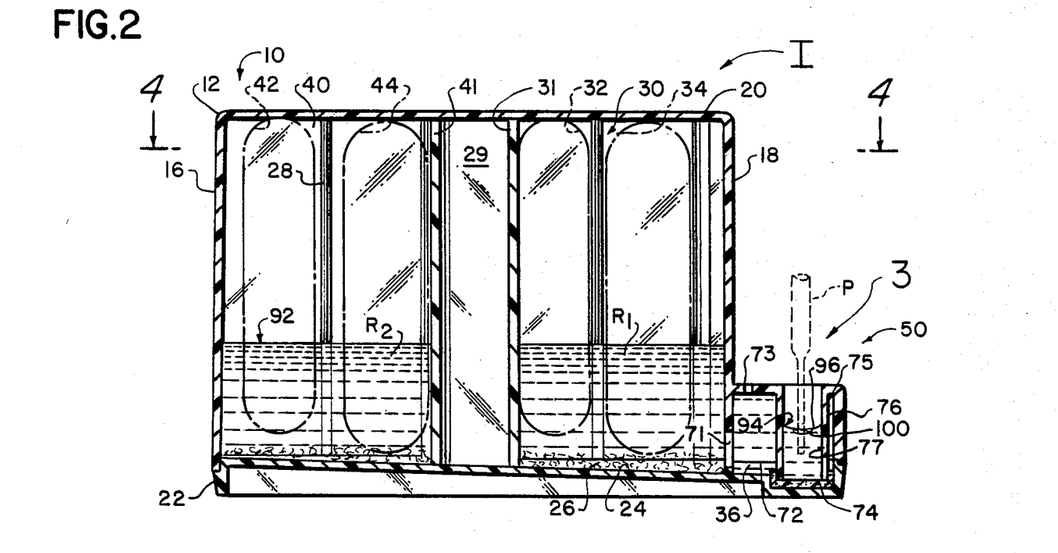
FIG. 2 is a cross-sectional view of the same embodiment of the integral reagent dispenser depicted in FIG. 1, shown here as prepared for use.

FIG. 2 shows a cross-section of two-reagent package I as prepared for use. To prepare dispenser package I for positioning of an immiscible liquid lens and liquid aspiration, it is tilted to rest on back wall 16, flexible side walls 14 are forced inwardly by external pressure, applied manually or by a suitably designed apparatus, to break capsules 32, 34, 42 and 44 and dispenser package I is gently rocked to reconstitute and mix each of the lyophilized reagent powders with its respective reconstituting liquid. After mixing, the dispenser package I is righted to the position shown in the drawing and can thereafter be positioned on a turntable, conveyor table or other transport means for use in an automated analysis system. Such a system can be, for example, the continuous flow system which is the subject of and more fully described in a cofiled application entitled, "SINGLE CHANNEL CONTINUOUS FLOW SYSTEM," having Ser. No. 441,881 and assigned to the instant assignee. The metering apparatus and method used during aspiration can be those which are the subject of and more fully described in a cofiled application entitled, "CONTINUOUS FLOW METERING APPARATUS," having also assigned to the instant assignee.

Reconstituted Ser. No. 441,720 reagent $R_1$ and $R_2$ liquids are made ready for aspiration, along with immiscible liquid, in identical manner. As such, the following description will refer to reagent $R_1$ liquid as exemplary. Reconstituted reagent $R_1$ liquid flows into $R_1$ dispenser component 70 to at least partially fill dispenser well 75. The continuous body of fluid between $R_1$ supply component 30 and $R_1$ dispenser component 70 reaches an equilibrium level, which is achieved by flow of reagent into dispenser component 70 until supply port 71 is occluded by the level of reagent liquid. Thus, an initial reservoir fluid level 92 and an initial dispenser well fluid level 94 are achieved for the continuous body of reconstituted reagent $R_1$ liquid. A concave reagent meniscus 97 is formed at the surface of reagent $R_1$ because of the hydrophilic inner surface 77 of dispenser well 75. A drop of immiscible liquid is dispensed onto this reagent surface, forming an immiscible liquid lens 100 which is centrally positioned thereon by the curvature of the meniscus. The drop of immiscible liquid can be dispensed manually, such as by pipet, or automatically, such as from an immiscible liquid dispenser component of an automated analysis system. The tip of a probe P (shown in phantom), which is a component of the analysis system and preferably made of a solid fluoropolymer sequentially intersects immiscible liquid lens 100 and reconstituted reagent $R_1$ liquid. Both segments of liquid are aspirated into the analysis system. Probe P can be provided with an immiscible liquid dispenser (not shown) having an applicator shroud, which dispenses immiscible liquid onto the outer surface thereof. The immiscible liquid introduced into probe P from lens 100 is replaced by the immiscible liquid flowing down the outer surface of probe P. The volume of immiscible liquid lens 100 is thereby kept substantially constant.

By repetition of the aspirating operation, a certain amount of reagent in dispensing well 75 is used up. As this occurs, the dispenser well fluid level 94 is lowered. When the level falls enough partially to expose supply port 71 to air, air flows into supply component 30 to replace that volume of reagent which is permitted to flow out into dispensing well 75. Vent hole 73 allows introduction of replacement air to supply component 30. Thus, the reagent level in dispensing well 75 remains within a narrow range until the supply of reagent $R_1$ is nearly depleted. Upon depletion, the unit is discarded.

Figure 3:
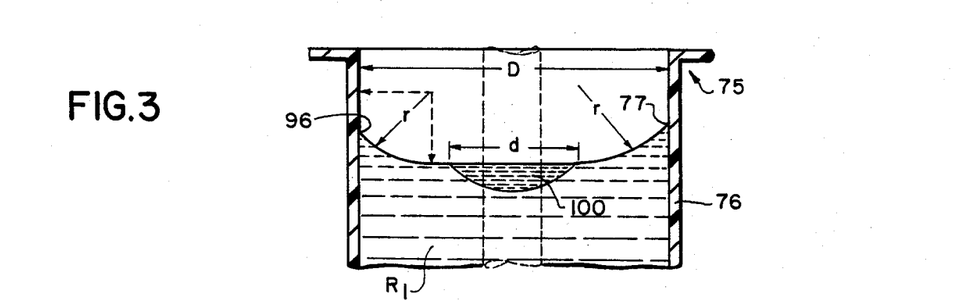
FIG. 3 is an enlarged partial view of the dispenser well of FIG. 2.

FIG. 3 is an enlarged partial view of that section of dispenser well 75 where the hydrophilic surface 77 of dispenser well wall 76 is in contact with the interface between reconstituted reagent $R_1$ liquid and air to form concave reagent meniscus 96. Dispenser well 75 has an inner diameter D which is at most about equal to the diameter d of immiscible liquid lens 100 plus twice the radius r of the curvature of reagent meniscus 96. In an example of this embodiment, well inner diameter D is 0.25 inches, diameter d of lens 100 is 0.10 inches and the radius r of concave reagent meniscus 96 is 0.08 inches.

Figure 4:
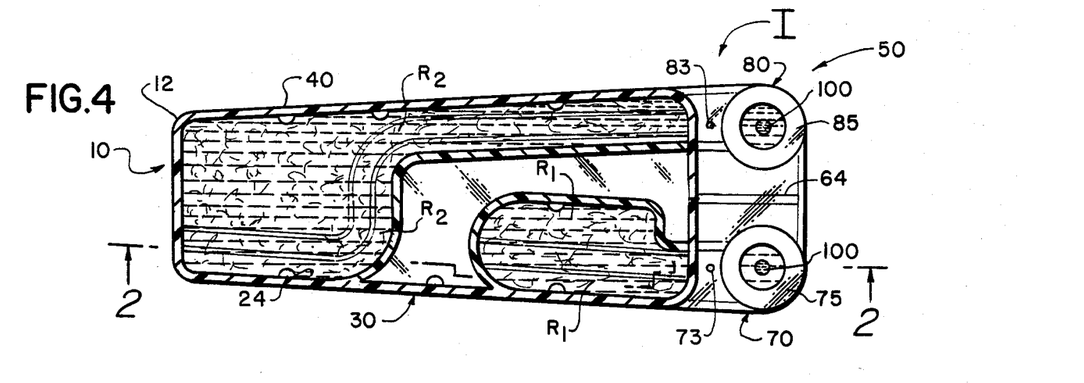
FIG. 4 is a top view of the integral reagent dispenser of FIG. 2.

FIG. 4 shows a top view of the two-reagent package I of FIG. 2. Reservoir housing 12 is shown to include reagent $R_1$ supply component 30 and reagent $R_2$ supply component 40 in which reconstituted reagent $R_1$ and reagent $R_2$ liquids are standing for supply to $R_1$ dispenser component 70 and $R_2$ dispenser component 80, respectively. Reagent $R_1$ and reagent $R_2$ liquids in dispenser components 70 and 80 are shown with an immiscible liquid lens 100 centrally positioned on the surface of each.

Figure 5:
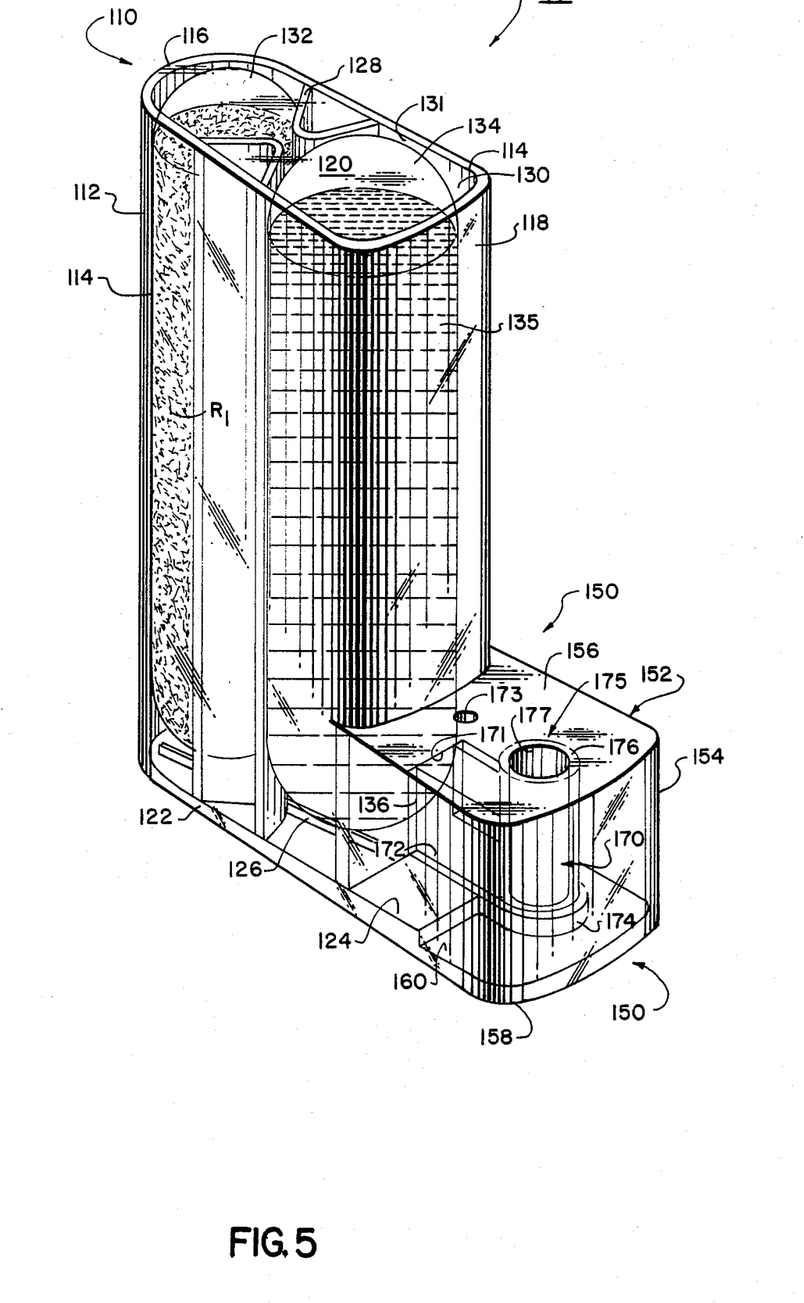
FIG. 5 is an isometric view of another preferred embodiment of the integral reagent dispenser of the invention.

FIG. 5 shows another preferred embodiment of the invention, a one-reagent dispenser II which includes a reagent reservoir assembly 110 having a reservoir housing 112 which encloses a supply component 130 for the single reagent to be dispensed. Reservoir housing 112 includes integral flexible side walls 114 which are continuous with back wall 116, front wall 118 and top 120. Reservoir housing 112 is fixed to base 122 by conventional adhesive or bonding techniques to form an enclosure. Base 122 provides the interior of the enclosure with an inclined floor 124 to maximize availability of reagent contents, shard fins 126 to insure against occlusion of openings in the package and support ribs 128 which provide desired structural rigidity at selected portions of housing 112.

Reagent $R_1$ supply component 130 comprises component wall 131, reagent $R_1$ capsule 132, which is filled with lyophilized reagent $R_1$ powder, reconstituting liquid capsule 134 which is filled with reconstituting liquid 135 and a supply trough 136. After appropriate package preparation, as described with reference to the previous embodiment, supply component trough 136 delivers reconstituted liquid reagent to a reagent dispenser assembly.

Stil referring to FIG. 5, reagent dispenser assembly 150 includes a dispenser housing 152 and a dispenser component for the reagent to be dispensed. Dispenser housing 152 includes housing wall 154, which forms an enclosure with top 156 and base 158. Base 158 is provided with a stepped floor 160, the step height of which is commensurate with the height of filter cup 178.

Reagent $R_1$ dispenser component 170 comprises a supply port 171, trough wall 172, vent hole 173, filter 174 and dispenser well 175, the interior of which is defined by dispenser well wall 176 having hydrophilic inner surface 177. As shown in later drawings, reagent $R_1$, which flows through supply port 171, is confined by trough wall 172 and thereby directed into the side of filter 174. From filter 174, it enters the interior of dispenser well 175, through the bottom, to present a standing volume of reagent $R_1$ liquid.

Figure 6:
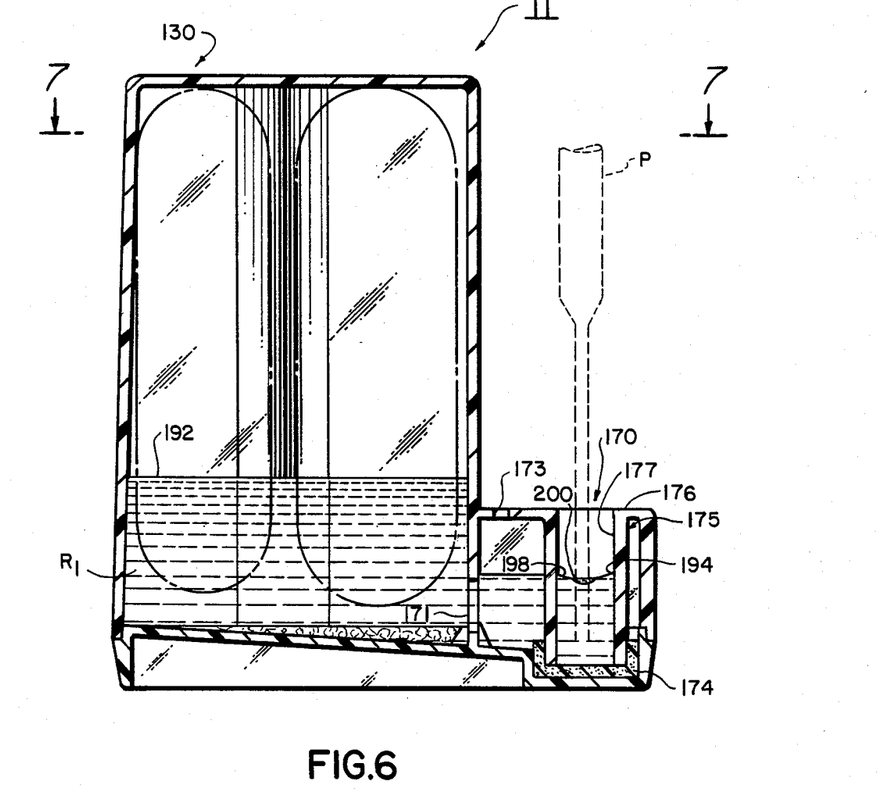
FIG. 6 is a cross-sectional view of the same embodiment of the integral reagent dispenser depicted in FIG. 5, shown here as prepared for use.

FIG. 6 shows a cross-section of the one-reagent package II, which has been prepared for use in the same way as the previously described embodiment. Reconstituted reagent $R_1$ liquid flows into $R_1$ dispenser component 170 to at least partially fill dispenser well 175. The continuous body of liquid between $R_1$ supply component 130 and $R_1$ dispenser component 170 reaches an equilibrium level, based on the same principal as in the previously described embodiment. Thus, a reservoir fluid level 192 and a dispenser well fluid level 194 are achieved for the continuous body of reconstituted reagent $R_1$ liquid. A concave reagent meniscus 198 is formed at the surface of the reagent $R_1$ liquid because of the hydrophilic inner surface 177 of dispenser well 175. A drop of immiscible liquid is dispensed onto this reagent surface, in the same manner as described for the previous embodiment forming an immiscible liquid lens 200, which is centrally positioned thereon by the curvature of the meniscus. The drop of immiscible liquid can be dispensed manually, such as by pipet, or automatically, such as from an immiscible liquid dispenser component of an automated analysis system. The tip of a probe P (shown in phantom), which is a component of the analysis system and preferably made of a solid fluoropolymer, sequentially intersects immiscible liquid lens 200 and reconstituted reagent $R_1$ liquid. Both segments of liquid are aspirated into the analysis systems. The volume of immiscible liquid lens 200 is maintained as described with reference to the previous embodiment.

By repetition of the aspirating operation, a certain amount of reagent in dispensing well 175 is used up. As this occurs, dispenser well fluid level 194 is also lowered. When this level falls enough to partially expose supply port 171 to air, air flows into supply component 130 to replace that volume of reagent which is permitted to flow out into dispensing well 175. Vent hole 173 allows introduction of air to supply component 130. Thus, the reagent level in the dispensing well remains within a range until the reagent supply is nearly depleted. Upon depletion, the unit is discarded.

Figure 7:
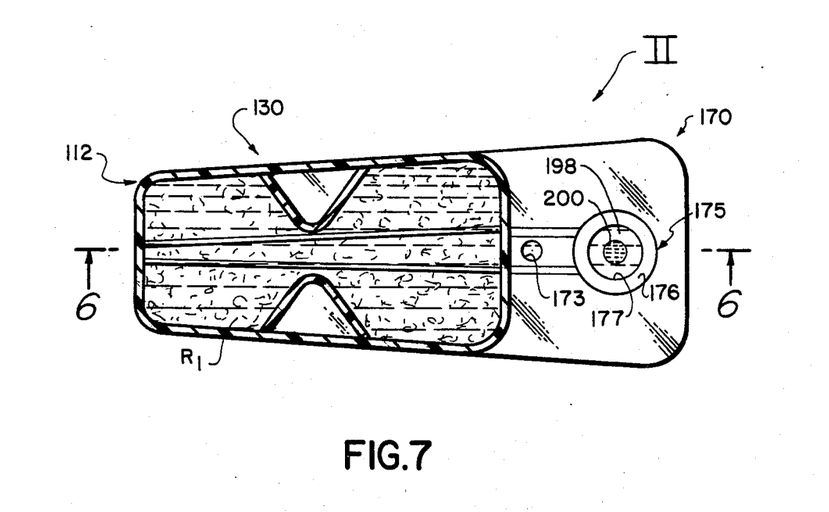
FIG. 7 is a top view of the integral reagent dispenser of FIG. 6.

FIG. 7 shows a top view of the two-reagent package II of FIG. 5. Reservoir housing 112 is shown to include reagent $R_1$ supply component 130 in which reagent $R_1$ liquid is standing for supply to $R_1$ dispenser component 170. The top surface of reconstituted reagent $R_1$ liquid are shown with immiscible liquid lens 200 centrally positioned on the surface.

Figure 8:
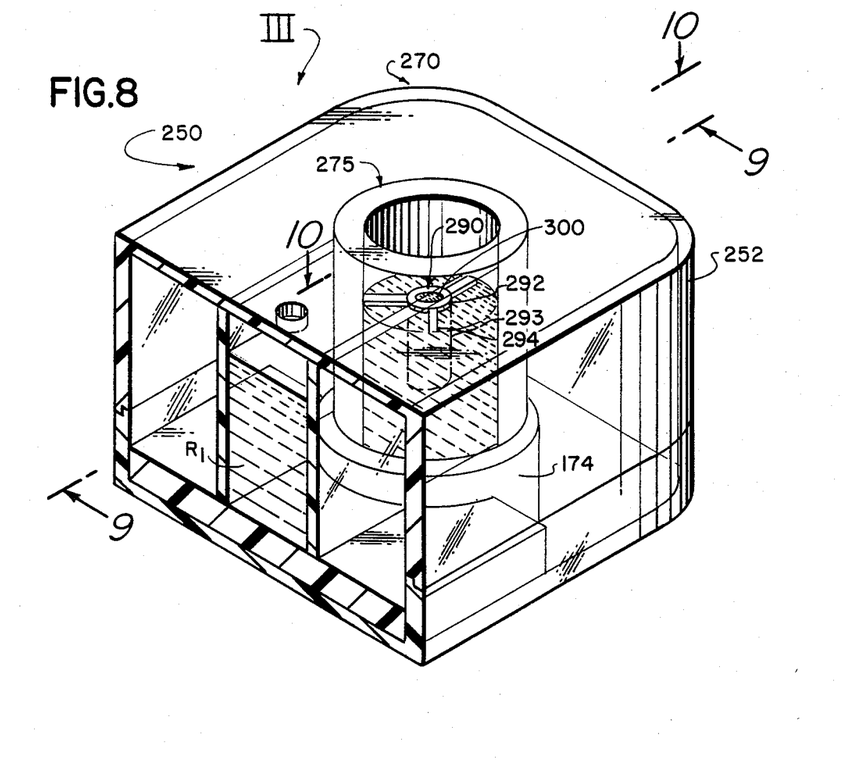
FIG. 8 is an enlarged partial view of another embodiment of the integral reagent dispenser of the invention which includes an immiscible liquid lens yoke.

FIG. 8 shows an enlarged partial view of another embodiment, integral reagent dispenser III, of the invention, which includes a reagent dispenser assembly 250 having a dispenser housing 252, a reagent dispenser component 270, holding a volume of reconstituted reagent $R_1$ liquid and an immiscible liquid lens yoke 290. Dispenser package III is prepared for positioning of an immiscible liquid lens and use in the same way as described for the previous embodiments. Lens yoke 290 includes a lens loop 292 which has a hydrophobic fluoropolymer inner surface and is, preferably, centrally positioned in dispenser well 275 of dispenser component 270 by support arms 294. Preferably, lens yoke 290 is integrally formed or molded of a material which is nonreactive with and floats on the reagent surface. Lens loop 292 is usually circular and has an inner diameter which is usually less than about 0.10 inches. Notably, the liquid reagent need not have a concave meniscus in this embodiment. Support arms 294 contact, but are not fixed to, dispenser well 275 in this embodiment. Immiscible fluid lens yoke 290 floats on the surface of reconstituted reagent $R_1$ liquid and thus vertically travels with it as the reagent level is lowered by repetition of the aspiration operation. Because support arms 294 can be of any desired number and each individually, of any desired length, a dispenser well is optional in this embodiment. For example, the support arms can extend directly from the inner surface of the dispenser housing, which can have any of a variety of different shapes. As shown in phantom, lens loop 292 can have downwardly extended walls to form an enclosure, lens cylinder 293, which maintains the position of immiscible liquid lens 300, as the reagent level is lowered, in examples where support arms 294 are fixed to dispenser well 275. Dispenser assembly 250 can be associated with any of a variety of reagent reservoir assemblies, particularly including those illustrated by and described with reference to earlier drawings. A filter or screen (not shown) can be positioned at the point of reagent liquid entry into dispenser component 270 when a dispenser well is not required or provided.

Figure 9:
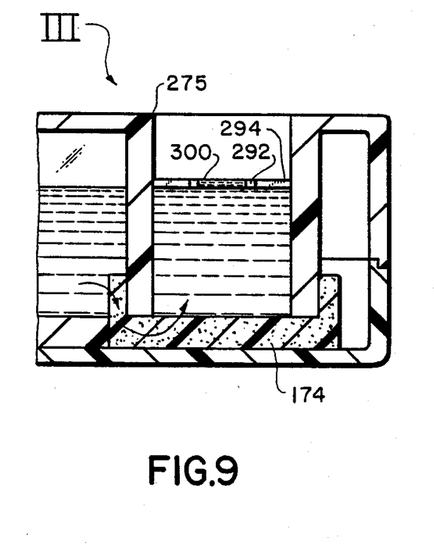
FIG. 9 is a cross-sectional view of the integral reagent dispenser of FIG. 8.

FIG. 9 shows a cross-section of the enlarged partial view of the single reagent package III of FIG. 8, as prepared for use and having an immiscible liquid lens 300 on the surface of the reagent. Support arms 294 extend transversely from lens loop 292 to the inner surface of dispenser well 275 at a level determined by that of reagent $R_1$ liquid. Notably, the surface of reagent $R_1$ does not form, and is not required to form, a curved meniscus.

Figure 10:
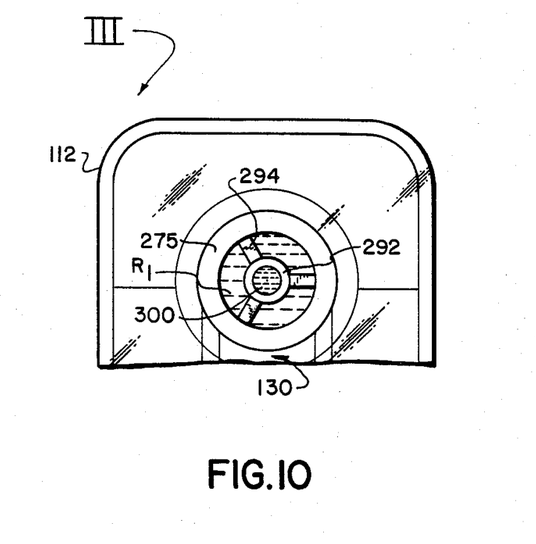
FIG. 10 is a top view of the integral reagent dispenser of FIG. 8.

FIG. 10 shows a top view of the reagent package III of FIG. 8. The top surface of reagent $R_1$ is shown with immiscible liquid lens 300 centrally positioned on the surface. Notably, the rotational position of each of support arms 294 has changed, illustrating that they are not fixed to the inner surface of dispenser well 275.

Although the invention has been described with particularly, numerous changes in the details, combinations and arrangement of elements may be resorted to without departing from the scope of the invention.

What is claimed is:

1. A unitary integral reagent container comprising:
   (a) means defining a plurality of reagent wells, each having a first opening for withdrawal of liquid reagent from said well therethrough and a second opening for introduction of liquid reagent into said well;
   (b) means for establishing a standing level of reagent in each of said reagent wells;
   (c) means comprising a reagent well interior cross-sectional area for maintaining a lens of immiscible liquid on the surface of said reagent and within a defined area of said surface when said reagent is contained in said reagent wells;
   (d) means defining a plurality of reagent reservoirs for containing a supply of liquid reagent in each, said reservoir defining means being integral with said reagent well defining means, wherein each such reagent reservoir cooperates with a selected reagent well;
   (e) means for repeatedly releasing a controlled amount of reagent liquid from each of said reagent reservoirs through an opening between each such reagent reservoir and the reagent well with which it cooperates and for introducing the controlled amount of reagent so-released into said cooperating reagent well through said second opening thereof.

2. The integral reagent container of claim 1 wherein each of said lens maintaining means comprises means for centrally positioning said lens on the reagent liquid surface.

3. The integral reagent container of claim 1 wherein each of said reagent reservoirs comprises a breakable capsule containing a reagent.

4. The integral reagent container of claim 1 wherein each reagent reservoir comprises a breakable capsule containing a dried reagent and a breakable capsule containing a reconstituting liquid.

5. The integral reagent container of claim 1 wherein each of said lens maintaining means comprises means for centrally positioning said lens on the reagent liquid surface.

6. The integral reagent container of claim 5 wherein each of said lens maintaining means comprises a reagent well hydrophilic inner surface providing a well inner diameter which is less than about 0.25 inch.

7. A unitary integral reagent container comprising:
   (a) means defining a reagent well having a first opening for withdrawal of liquid reagent from said well therethrough and a second opening for introduction of liquid reagent into said well;
   (b) means for establishing a standing level of reagent in said reagent well;
   (c) means comprising a reagent well interior cross-sectional area for maintaining a lens of immiscible liquid on the surface of such reagent and within a defined area of such surface when such reagent is contained in said reagent well;
   (d) means defining a reagent reservoir integral with said reagent well for containing a supply of reagent liquid; and
   (e) means for repeatedly releasing a controlled amount of reagent liquid from said reagent reservoir through an opening between said reagent reservoir and reagent well and for introducing the controlled amount of reagent so-released into said reagent well through said second opening thereof.

8. The integral reagent container of claim 7 wherein said lens maintaining means comprises means for centrally positioning said lens on the reagent liquid surface.

9. The integral reagent container of claim 7 wherein said lens maintaining means comprises a reagent well hydrophilic inner surface providing a well inner diameter which is at most about that of the diameter of the lens plus twice the radius of curvature of a meniscus produced by interaction of the reagent in the reagent well with the hydrophilic inner surface of the reagent well.

10. The integral reagent container of claim 1 wherein said dispenser well inner diameter is less than about 0.25 inch.

11. The integral reagent container of claim 7 wherein the reagent reservoir contains sufficient reagent to maintain the dispenser well reagent level within a range during repeated withdrawl of reagent therefrom.

12. The integral reagent container of claim 1 wherein said reagent reservoir comprises a breakable capsule containing a reagent.

13. The integral reagent container of claim 12 wherein said reagent is dried and said reagent reservoir further comprises a breakable capsule containing a reconstituting liquid.

14. The integral reagent container of claim 7 which further comprises a filter positioned along the reagent flow path between said reagent reservoir and said reagent well.

15. The integral reagent container of claim 14 wherein said filter is positioned at a reagent entrance to said reagent well.

16. The integral reagent container of claim 7 wherein the reagent reservoir is in fluid communication with the means defining a reagent well through a supply port.

17. The integral reagent container of claim 16 which further comprises means for passing reagent from said reagent reservoir to said means defining a reagent well through said supply port.

18. The integral reagent container of claim 7 wherein said means for establishing a standing reagent level comprises means for maintaining a substantially constant level of reagent liquid in said reagent well.

19. The integral reagent container of claim 18 which comprises means for passing air from said means defining a reagent well to said reagent reservoir.

20. The integral reagent container of claim 19 which includes a venthole in said means defining a reagent well to introduce air thereinto for replacement of air passing therefrom to said reagent reservoir.

21. A unitary integral reagent container which comprises:
  (a) means defining a reagent well;
  (b) means for establishing a standing level of reagent in said reagent well; and
  (c) means comprising a lens yoke having lens enclosure means and means for positioning said enclosure means for maintaining a lens of immiscible liquid on the surface of said reagent and within a defined area of said surface when said reagent is contained in said reagent well.

22. The integral reagent container of claim 21 wherein said reagent well has a first opening for withdrawal of a liquid reagent therethrough and has said lens maintaining means therein.

23. The integral reagent container of claim 21 wherein said reagent well is cylindrical.

24. The integral reagent container of claim 21 wherein said lens enclosure means is of a solid fluoropolymer.

25. The integral reagent container of claim 21 wherein said lens enclosure means is cylindrical.

26. The integral reagent container of claim 21 wherein said positioning means comprises at least one support arm extending from said lens enclosure means to said reagent well.

27. The integral reagent container of claim 21 which further comprises means defining a reagent reservoir integral and cooperating with said reagent well to supply liquid reagent thereto.

28. The integral reagent container of claim 27 wherein the reagent reservoir is in fluid communication with the means defining a reagent well through a supply port.

29. The integral reagent container of claim 27 wherein said means for establishing a standing reagent level comprises means for maintaining a substantially constant level of reagent liquid in said reagent well.

30. The integral reagent container of claim 27 wherein said reagent reservoir comprises a breakable capsule containing a reagent.

31. The integral reagent container of claim 30 wherein said reagent is dried and said reagent reservoir further comprises a breakable capsule containing a reconstituting liquid.

32. A unitary, integral reagent container comprising:
  (a) means defining a plurality of reagent wells;
  (b) means for establishing a standing level of reagent in each of said reagent wells; and
  (c) means comprising a lens yoke having lens enclosure means and means for positioning said enclosure means in said reagent wells for maintaining a lens of immiscible liquid on the surface of said reagent and within a defined area of said surface when said reagent is in said reagent wells.

33. The integral reagent container of claim 32 which further comprises:
  (d) means defining a plurality of reagent reservoirs for containing a supply of liquid reagent in each, said reservoir defining means being integral with said reagent well defining means, wherein each such reagent reservoir cooperates with a selected reagent well; and
  (e) means for repeatedly releasing a controlled amount of reagent liquid from each of said reagent reservoirs through an opening between each such reagent reservoir and the reagent well with which it cooperates and for introducing the controlled amount of reagent so-released into said cooperating reagent well through said second opening thereof.

34. The integral reagent container of claim 33 wherein each reagent reservoir is in fluid communication with a reagent well through a supply port.

35. The integral reagent container of claim 33 wherein said means for establishing a standing reagent level comprises means for maintaining a substantially constant level of reagent liquid in said reagent wells.

36. The integrel reagent container of claim 33 wherein each reagent reservoir comprises a breakable capsule containing a reagent.

37. The integral reagent container of claim 36 wherein said reagent is dried and each reagent reservoir further comprises a breakable capsule containing a reconstituting liquid.

38. An integral reagent container which comprises a reagent container housing and, therein:
  (a) first and second reagent wells, each having a first opening for withdrawal of liquid reagent from said well therethrough, a second opening for introduction of liquid reagent into said well, means for maintaining a lens of immiscible liquid on the surface of such reagent and within a defined area of such surface when such reagent is contained in said reagent well which means comprises a hydrophilic inner surface and an inner diameter of less than about 0.5 inch;
  (b) means for establishing a standing level of reagent in each of said reagent wells;
  (c) a first reagent reservoir which contains at least one reagent of a composition effective to detectably react with a sample and cooperates with said first reagent well to supply said at least one reagent thereto as a liquid; and
  (d) a second reagent reservoir which contains the remaining reagents of said composition and cooperates with said second reagent well to supply said remaining reagents thereto as a liquid;
  (e) means for repeatedly releasing a controlled amount of reagent liquid from said first and second reagent reservoirs through an opening between said reagent reservoir and the reagent well with which it cooperates and for introducing the controlled amount of reagent so-released into said reagent well through said second opening thereof.

* * * * *